United States Patent [19]

Avar et al.

[11] Patent Number: 5,705,545
[45] Date of Patent: Jan. 6, 1998

[54] USE OF HALS COMPOUNDS

[75] Inventors: Lajos Avar, Biel-Banken, Switzerland; Gilbert Ligner, Wintzenheim, France

[73] Assignee: Clariant Finance (BVI) Limited, Tortola, Virgin Islands (Br.)

[21] Appl. No.: 545,961

[22] Filed: Oct. 20, 1995

Related U.S. Application Data

[63] Continuation of Ser. No. 107,405, Aug. 16, 1993, abandoned.

[30] Foreign Application Priority Data

Aug. 17, 1992 [DE] Germany .................. 42 27 216.5

[51] Int. Cl.$^6$ ............................................ C08K 5/3435
[52] U.S. Cl. .................... 524/102; 526/263; 526/265
[58] Field of Search .................. 524/102; 546/187, 546/188, 190; 526/263, 265

[56] References Cited

U.S. PATENT DOCUMENTS 4,238,613  12/1980  Rasberger et al. ............... 546/190

FOREIGN PATENT DOCUMENTS 3412227  10/1984  Germany .

OTHER PUBLICATIONS

Leaversuch, "Polyolefins gain higher performance from new catalyst technologies", Modern Plastics, Oct. 1991.

*Primary Examiner*—Kriellion S. Morgan
*Attorney, Agent, or Firm*—Gabriel Lopez, Esquire

[57] ABSTRACT

A compound of formula I for use in stabilizing polymeric material against effects such as light and heat

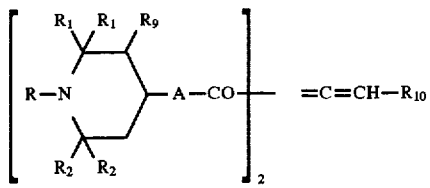

in which R is hydrogen; oxygen; —OH; $C_{1-24}$alkyl; —O—CO—$C_{1-24}$alkyl; —O—CO—$C_{1-24}$alkyl; —O—CO-phenyl or —COR$_5$; where R$_5$ is —C(R$_3$)=CH$_2$, $C_{1-6}$alkyl, phenyl, CO—$C_{1-24}$alkyl, —CO—phenyl, —NR$_7$R$_8$, —CH$_2$—C$_6$H$_5$, —CO—OC$_{1-12}$alkyl or —COOH; where R$_3$ is hydrogen or $C_{1-4}$alkyl; R$_7$ is hydrogen, $C_{1-12}$alkyl, $C_{5-6}$cycloalkyl, phenyl, phenyl-$C_{1-4}$alkyl or $C_{1-12}$alkylphenyl and R$_8$ is $C_{1-12}$alkyl or hydrogen, each R$_1$, independently, is —CH$_3$ or —CH$_2$($C_{1-4}$alkyl) or both groups R$_1$ form a group —(CH$_2$)$_5$—; and each R$_2$, independently, is —CH$_3$ or —CH$_2$($C_{1-4}$alkyl) or both groups R$_2$ form a group —(CH$_2$)$_5$—.

A is —O— or —N($C_{1-4}$alkyl)— or —NH—

R$_9$ is hydrogen or methyl, and

R$_{10}$ is an aromatic single ring or an aromatic fused 2 to 3 ring group or a heteroaromatic single ring or a a heteroaromatic fused 2 or 3 ring group.

21 Claims, No Drawings

USE OF HALS COMPOUNDS

This is a continuation of application Ser. No. 08/107,405, filed Aug. 16, 1993 abandoned.

The invention relates to hindered amine light stabilizer (HALS) compounds for use in stabilizing plastics material against effects such as light and heat. Many of these HALS compounds are new. The HALS compounds can also react or graft with the polymeric material According to the invention, there is provided a composition comprising a thermoplastic material and a compound of formula I

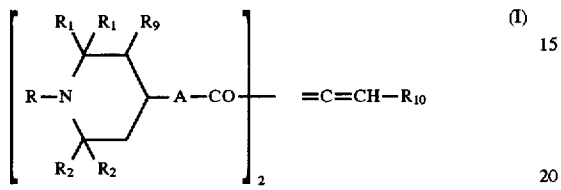

in which

R is hydrogen; oxygen; —OH; $C_{1-24}$alkyl; —O—$C_{1-24}$alkyl; —O—CO—$C_{1-24}$alkyl; —O—CO-phenyl or —$COR_5$; where $R_5$ is —$C(R_3)$=$CH_2$, $C_{1-6}$alkyl, phenyl, CO—$C_{1-24}$alkyl, —CO-phenyl, —$NR_7R_8$, —$CH_2$—$C_6H_5$, —CO—$OC_{1-12}$alkyl or —COOH; where $R_3$ is hydrogen or $C_{1-4}$alkyl; $R_7$ is hydrogen, $C_{1-12}$alkyl, $C_{5-6}$cycloalkyl, phenyl, phenyl-$C_{1-4}$alkyl or $C_{1-12}$alkylphenyl and $R_8$ is $C_{1-12}$alkyl or hydrogen, each $R_1$, independently, is —$CH_3$ or —$CH_2(C_{1-4}$alkyl) or both groups $R_1$ form a group —$(CH_2)_5$—; and each $R_2$, independently, is —$CH_3$ or —$CH_2(C_{1-4}$alkyl) or both groups $R_2$ form a group —$(CH_2)_5$—.

A is —O— or —$N(C_{1-4}$alkyl)— or —NH— (preferably —O—)

$R_9$ is hydrogen or methyl, preferably hydrogen and $R_{10}$ is an aromatic single ring or an aromatic fused 2 or 3 ring group or a heteroaromatic single ring or a heteroaromatic fused 2 or 3 ring group.

Preferably the amount of the compound of formula I added is 0.01–5%, more preferably 0.05 to 2.5% most preferably 0.1 to 0.5% based on the weight of thermoplastic material.

Preferably $R_{10}$ is $R_{10}'$ where $R_{10}'$ is phenyl, unsubstituted or substituted by one to three groups selected from $C_{1-8}$alkyl, $C_{1-8}$alkoxy and —OH or by one or two (preferably two) substituents selected from a group of formula α

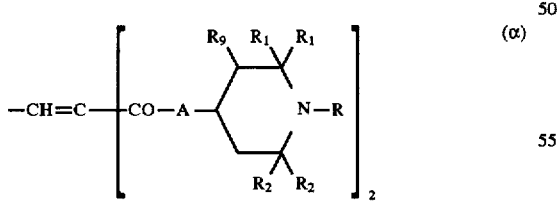

or $R_{10}'$ is napthyl or a group selected from groups of formula a–h:

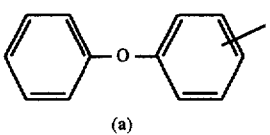

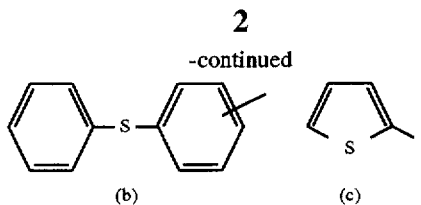

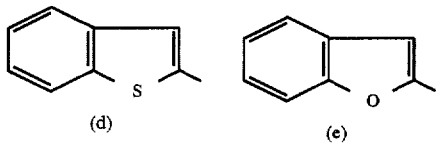

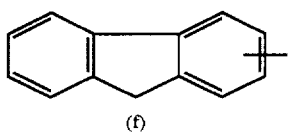

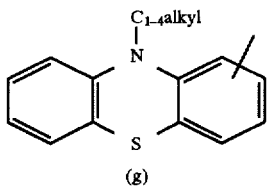

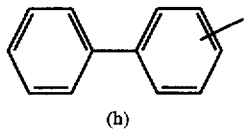

More preferably $R_{10}$ is $R_{10}''$ where $R_{10}''$ is phenyl, unsubstituted or substituted by one to three groups selected from $C_{1-8}$alkyl, $C_{1-8}$alkoxy and OH (maximum one —OH), [especially

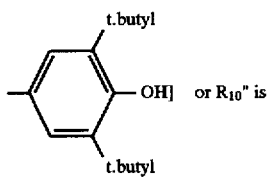

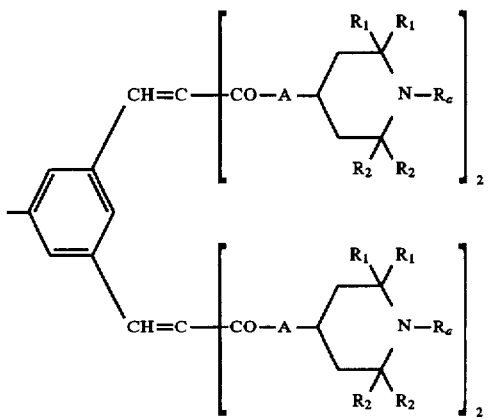

Preferred compounds of formula I are of formula Ia

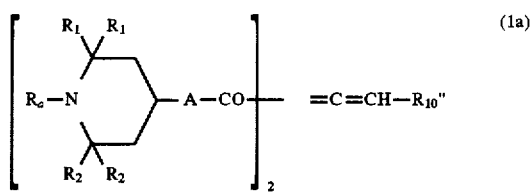

where $R_a$ is hydrogen, $C_{1-8}$alkoxy, hydroxy or —CO—$R_5$' is —CH=CH$_2$, $C_{1-4}$alkyl or —CO—O—$C_{1-4}$alkyl;

$R_{10}''$ is phenyl, unsubstituted or substituted by one to three groups selected from $C_{1-8}$alkyl, $C_{1-8}$alkoxy and OH (max. one OH) or $R_{10}''$ is a group of formula b)

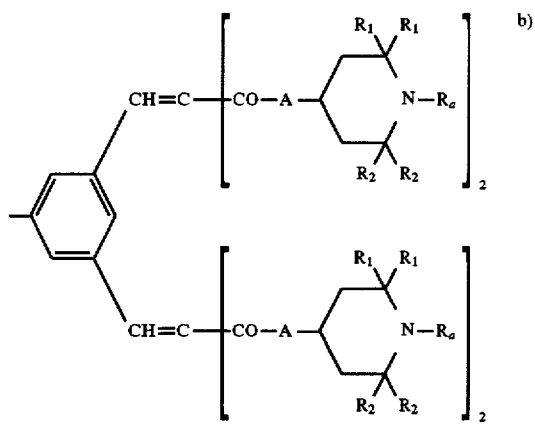

More preferred compound of formula I are of formula Ib

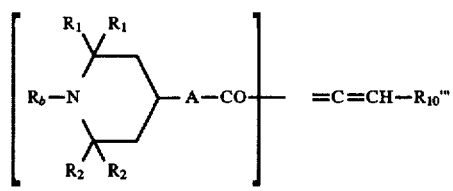

where $R_b$ is hydrogen, $C_{1-4}$alkyl, hydroxyl or $C_{1-4}$alkoxy and $R_{10}'''$ is phenyl, unsubstituted or substituted by one to three groups selected from $C_{1-4}$alkyl, $C_{1-8}$alkoxy and —OH or $R_{10}'''$ is a group of formula b)

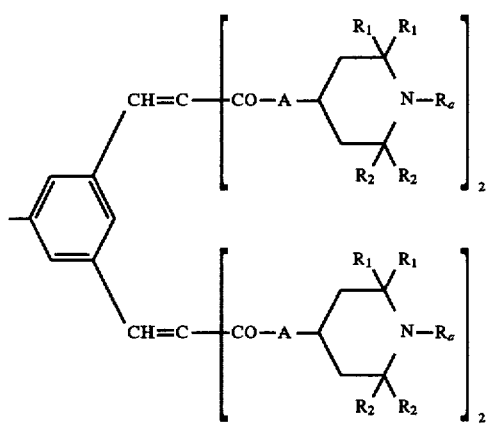

where the symbols are defined above.

Most preferred compounds of formula I are of formula Ic

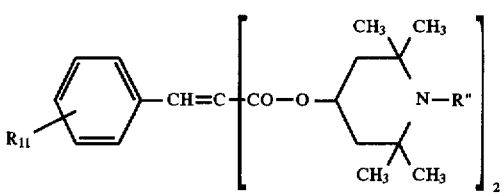

in which $R_{11}$ is $C_{1-4}$alkyl, $C_{1-4}$alkoxy or hydrogen; and

R" is hydrogen, $C_{1-4}$alkyl or $C_{1-8}$alkoxy $R_{11}$ is preferably $R_{11}'$ in which $R_{11}'$ is methoxy, ethoxy or hydrogen Most preferably $R_{11}$ is in the 4-position R" is preferably R'" where R'" is hydrogen, methyl or $C_{1-8}$alkoxy (e.g. methoxy, ethoxy or especially —O—C$_8$H$_{17}$)

In $R_{10}$, any $C_{1-8}$alkyl groups are preferably $C_{1-4}$alkyl, more preferably methyl or ethyl.

In $R_{10}$ any $C_{1-8}$alkoxy is preferably methoxy, ethoxy or n-octyloxy.

Compounds of formula I are new, with the proviso that when $R_{10}$ is paramethoxyphenyl, R is not hydrogen. Preferably in such new compounds, when $R_{10}$ is alkoxy phenyl, R is not hydrogen. Most preferably in the new compounds of formula I, R is not hydrogen.

Compounds of formula I can be prepared by condensing one mole of a compound of formula II

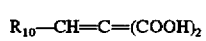

(or a derivative thereof e.g. $C_{1-4}$alkyl ester or the acid halide) with 2 moles of a compound of formula III

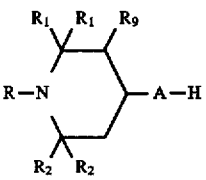

at elevated temperatures (generally 80°–200° C.).

Compounds of formula II and III are known or may be made from known compounds by known methods.

A compound of further interest is of formula Id

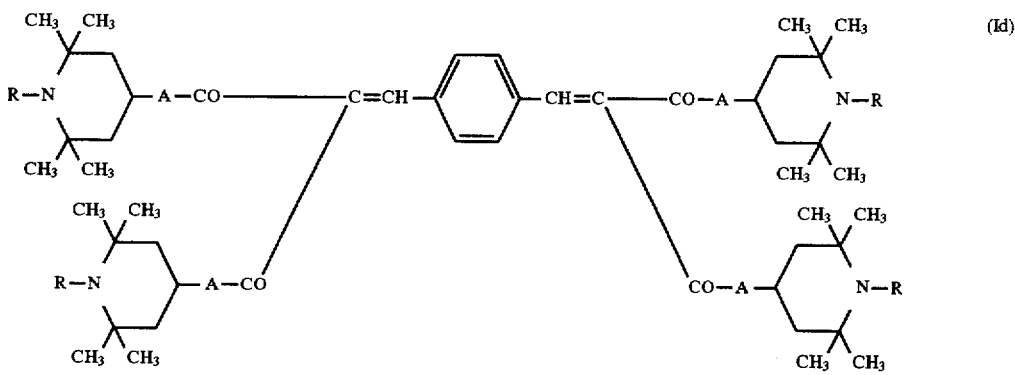

The preparation of the compound of formula Id is carried out by reacting one mol of the compound of formula IV

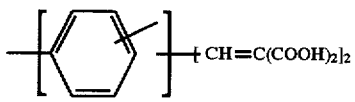

or a derivative thereof with 4 mols of a compound of formula III.

The compounds of formula I are especially suitable for stabilizing polyolefins especially polypropylene, polyethylene (e.g. high density polyethylene, low density polyethylene, linear low density polyethylene or medium density polypropylene) polybutylene, poly-4-methylpentene and of special interest are the α-polyolefins prepared using processing catalysts known as Generation II to Generation V catalysts and which have not been subjected to a catalyst removal step. By the term "catalyst removal step" used herein is meant a step for the purpose of positively removing the catalyst residues contained in the polymerized polyolefins or treating the polyolefins with the compound which can react with the catalyst residue and inactivate or solubilize the residue, such as alcohols or water, and then removing the inactivated or solubilized catalyst residue by physical means such as filtration, washing and centrifuging. Thus, in the case of suspension polymerization, the step of separating the resulting polymer from a dispersion medium, such as a solvent or a liquefied monomer, does not fall under the above-mentioned definition of the catalyst residue removal step, although the catalyst dissolved in the dispersion medium may be removed by a separation step.

The step of adding a small amount of catalyst poisons such as ethers, alcohols, ketones, esters and water to the resulting polymer, to inactivate the catalyst remaining after the completion of polymerization, or the step of treating the resulting polymer suspension with gas such as steam or nitrogen to remove the dispersion medium also does not fall under the above-mentioned definition of the "catalyst residue-removal" step.

What we mean by Generation I catalysts are titanium halide catalysts and an organo aluminium compound or an organo aluminium halide.

What we mean by Generation II catalysts are Generation I catalysts supported on an organo magnesium compound or based on an organo chromium compound supported on SiO2.

What we mean by a Generation III catalyst is a Ziegler type complex catalyst supported on a halogen containing magnesium compound.

What we mean by a Generation IV catalyst is a Generation III catalyst with a silane donor.

What we mean by Generation V catalysts is a bis-indenyl organo titanium compound supported an alumoxane or bis cyclopentadienyl titanium halides activated by aluminium alkyl compound.

Further generations of highly specific catalysts, especially useful for manufacturing highly stereoregular poly-α-olefins, which are presently under development, belong in the sense of the present invention also to the aforementioned generations of supported catalyst systems. Examples for the microstructure of such highly stereoregular polyolefins are given by syndiotactic polypropylene, iostactic stereoblock polymers, iostactic polypropylene containing stearic defects randomly distributed along the polymer chain (so called anisotactic polypropylene) or stereoirregular steroblock polymers. Due to the rapid progress in the development of newer generation catalyst systems the commercial significance of these polymers with novel, highly interesting properties increases more and more. However, residues of such further catalyst generations, as long as they contain metals of the 3d, 4d and 5d series of the periodic system supported analogously to the earlier catalyst generations, can also cause disadvantageous properties in the polymer, as long as such residues are still present in the polymer even if in a deactivated form.

Due to this, it can therefore be expected that the new compositions according to the invention are also suitable for overcoming such disadvantageous properties of the polymer. This means that any disadvantageous interaction between processing stabilizers and the aforementioned residues of catalysts of further generations, particularly the hydrolysis of phosphites and phosphonites, is most effectively inhibited.

These generations of catalysts are described in the Twelfth Annual International Conference on Advances in the stabilization and Controlled Degradation of Polymers held in Luzern, Switzerland, 21–23 May 1990 in an article on pages 181 to 196 inclusive by Rolf Mülhaupt entitled "New Trends in Polyolefin Catalysts and Influence on Polymer Stability". The contents of this article is incorporated herein by reference and especially Table I on page 184 describing the Generation of Catalysts:

TABLE I

Polyolefin Catalyst Evolution

| | Generation Example | Cat. Act. % | Act. Ti (g/PP/g Ti hatm) | Stereoreg. (% insol in heptane) | Process Technology |
|---|---|---|---|---|---|
| I | TiCl$_4$/AlR$_3$ | 40 | 0.01 | 45% | removal of cat. residues and atactic PP |
| | TiCl$_3$/AlEt$_2$Cl | 30 | 0.1 | 92% | removal of catalyst residues |
| II | Mg(OEt$_2$)/TiCl$_4$/AlR$_3$ SiO$_2$/Cp$_2$Cr | 40000 40000 | HPDE | 50% | no removal of cat. residues (mainly HDPE/LLDPE) |
| III | Mod. TiCl$_3$ cat. MgCl$_2$/TiCl$_4$/AlR$_3$- ester donor | 5000 20000 | 1 10 | 95% 92% | no purification |
| IV | MgCl$_2$/TiCl$_4$/AlR$_3$- silane donor | 40000 | 18 | 99% | no purification no extrusion |
| V | Bis-indenyl-TiR$_2$ on (AlCH$_3$O)$_2$ | 40000 | 100 | 99% | novel PPs, narrow MWD | in which R, in Table 1, is an organo group, HDPE is high density polyethylene, LLDPE is linear low density polyethyene, Cp is cyclopentadienyl, Et is ethyl, PP is polypropylene and MWD is molecular weight distribution.

Further additives that can be added to a composition according to the invention include antioxidants, such as sterically hindered phenols, secondary aromatic amines or thioethers, such as described in "Kunststoff-Additive"—G ächter/Müller, Ed. 3, 1990 p.42–50, the contents of which are incorporated herein by reference;acid scavengers such as sodium-, magnesium-or calcium- stearates or lactates, hydrotalcite or alkoxylated amines; U.V. stabilizers such as sterically hindered amines (for example N-unsubstituted, N-alkyl or N-acyl substituted 2,2,6,6-tetra-methylpiperidine compounds) [also known as hindered amine light stabilizers-HALS] and U.V. absorbers (e.g. 2-(2'-hydroxyphenyl)-benztriazoles, 2-hydroxy-benzophenones, 1,3-bis-(2'-hydroxybenzoyl) benzene salicylates, cinnamates and oxalic acid diamides;), U.V. quenchers such as benzoates and substituted benzoates, antistatic agents, flameproofing agents, lubricants, plasticisers, nucleating agents, metal deactivators, biocides, impact modifiers, fillers, pigments and fungicides.

The compounds of formula I when added to polymeric material (preferably material having one or more unsaturated groups present) have been found to react or graft either totally or at least in part to the polymeric material (especially plastic material) and generally only react in the presence of U.V. light. This is especially true when the polymeric material is a polyolefin.

Still further, therefore according to the invention there is provided a polymeric material containing a 2,2,6,6-tetraalkylpiperidinyl group derived from a compound of formula I that has been reacted with or grafted into the polymeric material. By the term "derived" is meant that group that results from the reaction of a compound of formula I with a polymeric material or with monomer capable of forming the said polymeric material.

Preferably the polymeric material is a thermoplastic material.

Further according to the invention there is provided a process for reacting a 2,2,6,6-tetraalkyl-piperidinyl compound with (or grafting into) a polymeric material comprising reacting (or grafting) a compound of formula I with a polymer (preferably having one or more unsaturated groups present) or one or more unsaturated monomers capable of reacting with a compound of formula I and exposing this to light.

Preferably the polymeric material is a thermoplastic material.

Preferably such a process is catalyzed by U.V. or visible light by exposing the HALS containing polymers or monomeric compositions for up to 500 hours, more preferably for 100–400 hours.

The polymeric material can further be stabilized by adding a phenolic antioxidant. In such a case from 0.01 to 0.2% (especially about 0.1%) of phenolic antioxidant based on the weight of polymeric material is added. Examples of such phenolic antioxidants are Irganox 1010

A further additive that can be added to calcium stearate. This is preferably added in an amount of 0.01 to 0.2%, especially 0.1% based on the weight of polymer in the polymeric material.

The compounds of formula I may be added during polymer formation by adding it to the monomeric material from which the polymeric material can be formed. It may also, however, be added to the polymeric material when it is being made up into a coating material (e.g. during coating lacquer formations)

Polyolefin especially polypropylene is the preferred polymeric material to which the compounds of formula I may be added. In such a case, the compounds of formula I can be mixed with powdered polymeric material, melted and then worked in formed articles (e.g. fibers, threads,films bands on thin plates) in which the grafting reaction may be performed by exposure to visible light or light in the near U.V.

Polymer articles of large size can also be formed from a polymeric material with which a 2,2,6,6-tetraalkylpiperidinyl compound derived from a monomer of formula I The polymeric substrate, (e.g. polypropylene) can contain other stabilizers especially light stabilizers e.g. U.V. absorber radical scavengers (e.g. HALS). Examples of such stabilizers are oxalanilides, benzotriazoles, 2-hydroxybenzophenones, 2-hydroxyphenyl-S-triazines and HALS such as Tinuvin 770, Tinuvin 944 or Tinuvin 946.

The invention will now be illustrated by the following Examples in which all parts and percentages are by weight and all temperatures are in °C. unless indicated to the contrary.

EXAMPLE 1

84 parts of para-methoxy benzalmalonic acid dimethyl-ester are added to 154 parts of 1,2,2,6,6-pentamethyl-4-hydroxypiperidine in 80 parts of xylene.

This is heated to 80° C. and reacted with 0.5 parts by volume of tetraisopropyl orthotitanate and, whilst distilling off the resulting methanol, the reaction mixture is stirred at 140° C. for 22 hours. The reaction mixture is cooled to 80°

C. washed thrice with water. The organic phase is separated off, the solvent is distilled off and the residue is recrystalized from ethanol. The resulting product of formula 1a

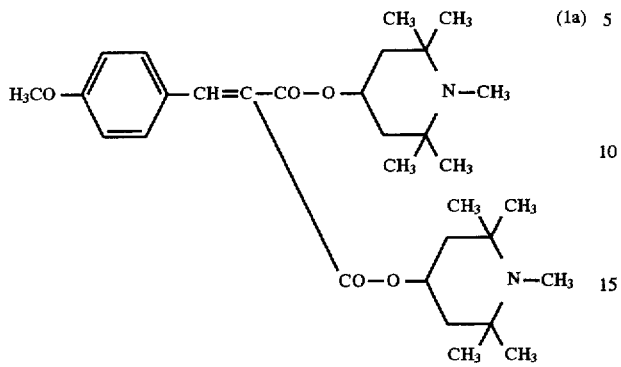

which melts at 121°–123° C.

EXAMPLE 2

20.9 parts of the tetraethylester of the compound of formula 2b

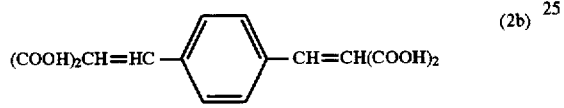

28 parts of 1,2,2,6,6-pentamethyl-4-hydroxypiperidine, 110 parts of xylene and 0.8 parts by volume of tetraisopropyl orthotitanate are reacted according to the procedure of Example 1. The resulting product of formula 2a

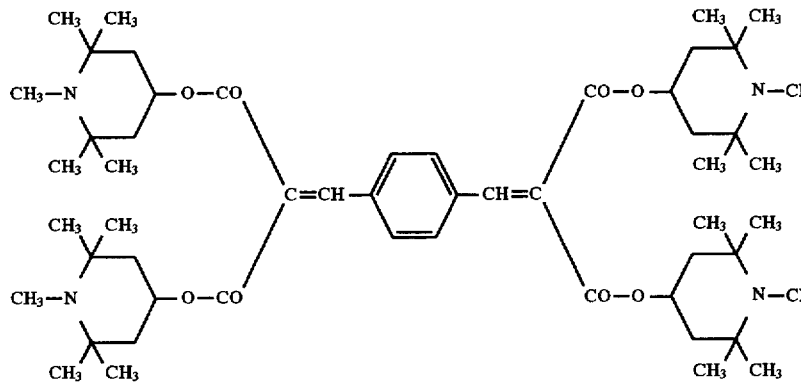

having a melting point of 234°–238° C.

EXAMPLE 3

By an analogous method to that of Example 1, benzalmalonic acid diethylester and 1,2,2,6,6-pentamethyl-4-hydroxypiperidine are reacted. The resulting product has a melting point of 95°–96° C.

EXAMPLE 4 TO 6

By a method analogous to that of Example 1

25.9 parts of 4-methoxy benzalmalonic acid dichloride (prepared from 4-methoxybenzylmalonic acid and thionylchloride) is dissolved in xylene(water-free) and is then is condensed with Example 4—98 parts of 2,2,6,6-tetramethyl-4-aminopiperidine Example 5—11.0 parts of 1,2,2,6,6-pentamethyl-4-aminopiperidine Example 6—12.5 parts of 1 formyl-2,2,6,6-tetramethyl-4-aminopiperidine

EXAMPLES 7–11

By a method analogous to that of Example 1

18.8 parts of 1,2,2,6,6-pentamethyl-4-hydroxypiperidine are reacted with

Example 7—18.8 parts of 3,5-ditert.butyl-4-hydroxy benzal-malonic acid diethyl ester Example 8—14.4 parts of 3,4-dimethoxy-benzalmalonic acid diethyl ester Example 9—13.8 parts of 4-methyl-mercapto benzalmalonic acid diethylester Example 10—16.2 parts of 4-phenylbenzalmalonic acid diethyl ester Example 11—12.7 parts of 1-thienyl-2')-2-bis(ethoxycarbonyl)ethylene

EXAMPLES 12–14

By a method analogous to that of Example 2, 21.2 parts of a compound of the formula

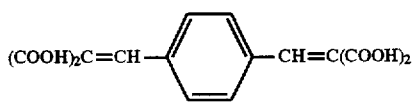

are reacted with

Example 12—25 parts of 2,2,6,6-tetramethyl-4-hydroxy piperidine

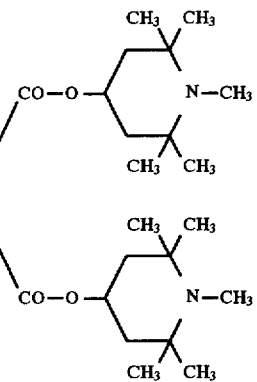

Example 13—28 parts of 1,2,2,6,6-pentamethyl-4-hydroxypiperidine

Example 14—31 parts of 1-acetyl-2,2,6,6-tetramethyl-4-hydroxypiperidine

EXAMPLES 15 AND 16

By a method analogous to that of Example 1, 84 parts of para-methoxybenzalmalonic acid dimethyl ester are reacted with Example 15—160 parts of 1-methoxy-2,2,6,6-tetramethyl-4-hydroxypiperdine Example 16—180 parts of 1-actyloxy-2,2,6,6-tetramethyl-4-hydroxypiperidine

Application Example

Commercially available polypropylene in powdered form, base stabilized with 0.1% of calcium stearate and 0.1% of a phenolic antioxidant (Irganox 1010 from Ciba-Geigy) is mixed with 0.1% of the compound of formula 1a (of Example 1). The mixture is melted and then formed into a sheet 0.1 mm thick. Two samples of this sheet are then exposed to a Xenon lamp one for 50 hours and the other for 200 hours. These two samples together with a sample of unexposed sheet are eluted in dichloromethane and the eluate is evaluted to see how much compound of formula 1a is present.

The results show that from the unexposed sample all the compound of formula 1a can be extracted; from the sample exposed for 50 hours only 10% can be extracted; and from the sample exposed for 200 hours no compound of formula 11 can be extracted.

The Application Example can be repeated using 0.1% of any one of the HALS stabilizors of Example 2–16 in place of the compound of formula 1a

[In the Application Example, all % are by weight of the polypropylene being stabilized]

The samples which have been exposed to light (and therefore, it is believed, have HALS derived from the compound of formula 1a grafted out to polypropylene) are as light stable as those in which the HALS is not chemically grafted to the polypropylene.

The Application Example can be repeated using 0.1% of any one of the HALS products of Example 2 to 16 in place of 0.1% of the compound of formula 1a.

What is claimed is:

1. A composition comprising a thermoplastic material and a compound of formula I

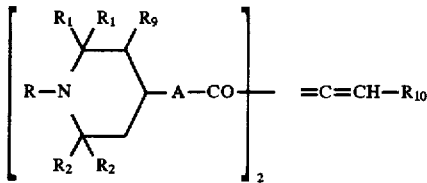

in which

R is $CH_3$;

each $R_1$, independently, is —$CH_3$ or —$CH_2(C_{1-4}alkyl)$ or both groups $R_1$ form a group —$(CH_2)_5$—;

each $R_2$, independently, is —$CH_3$ or —$CH_2(C_{1-4}alkyl)$ or both groups $R_2$ form a group —$(CH_2)_5$—;

$R_9$ is hydrogen or methyl;

$R_{10}$ is methoxyphenyl; and

A is —O—, —$N(C_{1-4}alkyl)$—, or —NH—.

2. A composition according to claim 1 in which $R_{10}$ is 4-methoxyphenyl.

3. A composition according to claim 2 wherein each $R_1$ and $R_2$ is methyl;

$R_9$ is H; and

A is —O—.

4. A composition according to claim 1 in which 0.01–5% of the compound of formula I are present based on the weight of thermoplastic material.

5. A process for reacting a 2,2,6,6-tetraalkyl-piperidinyl compound with a polymeric material comprising the process step of: reacting a compound of formula I according to claim 1 with a polymeric material having one or more unsaturated monomers capable of reacting with a compound of formula I.

6. A process of claim 5 further comprising catalyzing said reaction by exposure to light.

7. A process for grafting 2,2,6,6-tetraalkyl-piperidinyl compound into a polymeric material comprising the process step of: grafting a compound of formula 1 according to claim 1 into a polymeric material having one or more unsaturated monomers capable of reacting with a compound of formula 1.

8. A process of claim 7 further comprising catalyzing said reaction by exposure to light.

9. A compound of formula I

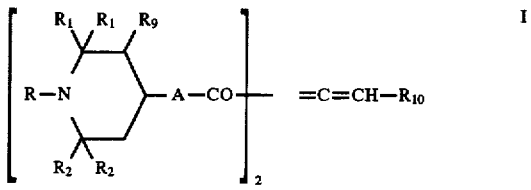

in which

R is $CH_3$;

each $R_1$, independently, is —$CH_3$ or —$CH_2(C_{1-4}alkyl)$ or both groups $R_1$ form a group —$(CH_2)_5$—;

each $R_2$, independently, is —$CH_3$ or —$CH_2(C_{1-4}alkyl)$ or both groups $R_2$ form a group —$(CH_2)_5$—;

$R_9$ is hydrogen or methyl;

$R_{10}$ is methoxyphenyl; and

A is —O—, —$N(C_{1-4}alkyl)$—, or —NH—.

10. A compound according to claim 9 in which $R_{10}$ is 4-methoxyphenyl.

11. A compound according to claim 10 wherein each $R_1$ and $R_2$ is methyl;

$R_9$ is H; and A is —O—.

12. A process for preparing a compound of formula I

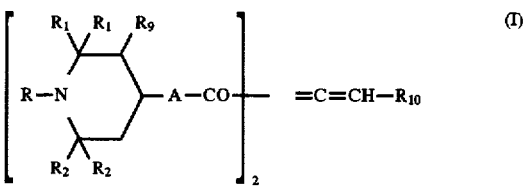

in which

R is hydrogen, oxygen, —OH, $C_{1-24}alkyl$, —O—$C_{1-24}alkyl$, —O—CO—$C_{1-24}$, —O—CO-phenyl, or —$COR_5$;

each $R_1$, independently, is —$CH_3$ or —$CH_2(C_{1-4}alkyl)$, or both groups $R_1$ form a group —$(CH_2)_5$;

each $R_2$, independently, is —$CH_3$ or —$CH_2(C_{1-4}alkyl)$ or both groups $R_2$ form a group —$(CH_2)_5$—;

$R_3$ is hydrogen or $C_{1-4}alkyl$;

$R_5$ is —$C(R_3)$=$CH_2$, $C_{1-6}alkyl$, phenyl, CO—$C_{1-24}alkyl$, —CO-phenyl, —$NR_7R_8$, —$CH_2$—$C_6H_5$, —CO—$OC_{1-12}alkyl$, or —COOH;

$R_7$ is hydrogen, $C_{1-12}alkyl$, $C_{5-6}cycloalkyl$, phenyl, phenyl-$C_{1-4}alkyl$, or $C_{1-12}alkylphenyl$;

$R_8$ is $C_{1-12}alkyl$, or hydrogen;

$R_9$ is hydrogen or methyl;

$R_{10}$ is an aromatic single ring, an aromatic fused 2 or 3 ring group, or a group of the formula

(c)

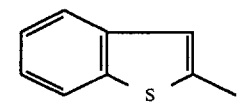
(d)

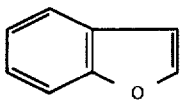 or
(e)

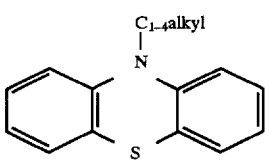 ; and
(g)

A is —O—, —N($C_{1-4}$alkyl)—, or —NH— comprising the process step of:

condensing one of mole of a compound or a derivative thereof of the formula II $R_{10}$—CH=C=(COOH)$_2$     II with 2 moles of a compound of formula III

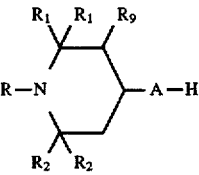     III

13. A process of claim 12 wherein said condensing is at temperatures of 80°–200° C.

14. A polymeric material containing a 2,2,6,6-tetraalkylpiperidinyl group derived from a compound of formula I according to claim 1 that has been reacted with or grafted with a polymeric material having one or more unsaturated monomers capable of reacting with a compound of formula I.

15. A composition of claim 1 wherein $R_9$ is methyl.

16. A composition of claim 1 wherein A is —N($C_{1-4}$alkyl)— or —NH—.

17. A compound of claim 9 wherein $R_9$ is methyl.

18. A compound of claim 9 wherein A is —N($C_{1-4}$alkyl)— or —NH—.

19. A process of claim 12 wherein $R_{10}$ is methoxy.

20. A process of claim 19 wherein each $R_1$ and $R_2$ is methyl, $R_9$ is H, and A is —O—.

21. A process of claim 12 wherein $R_9$ is methyl and A is —N($C_{1-4}$alkyl)— or —NH—.

* * * * *